United States Patent [19]
Tadano et al.

[11] Patent Number: 5,962,248
[45] Date of Patent: *Oct. 5, 1999

[54] QUANTITATIVE DETERMINATION METHOD FOR CHLORIDE IONS

[75] Inventors: Toshio Tadano, Shizuoka; Norihiko Kayahara, Kanagawa; Jun Umemoto, Hyogo, all of Japan

[73] Assignee: Kyowa Medex Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/586,785
[22] PCT Filed: Aug. 3, 1994
[86] PCT No.: PCT/JP94/01279
 § 371 Date: Jan. 23, 1996
 § 102(e) Date: Jan. 23, 1996
[87] PCT Pub. No.: WO95/04831
 PCT Pub. Date: Feb. 16, 1995

[30] Foreign Application Priority Data

Aug. 4, 1993 [JP] Japan ..................................... 5-193728

[51] Int. Cl.⁶ ...................................................... C12Q 1/40
[52] U.S. Cl. ................................... 435/22; 435/14; 435/15
[58] Field of Search ............................... 435/14, 15, 7.22, 435/22, 962

[56] References Cited

U.S. PATENT DOCUMENTS

| | | | |
|---|---|---|---|
| 4,427,771 | 1/1984 | Misaki et al. | 435/22 |
| 5,384,247 | 1/1995 | Berry et al. | 435/22 |
| 5,719,036 | 2/1998 | Tadano et al. | 435/26 |

OTHER PUBLICATIONS

Levitzki A., The Allosteric Activation of Mammalian Amylase by Chloride, Eur J Biochem 41 171–180, 1974.

Ono T., A New Enzymatic Assay of Chloride in Serum, Clin Chem 34(3) 552–553, 1988.

*Primary Examiner*—Ralph Gitomer
*Attorney, Agent, or Firm*—Fitzpatrick, Cella, Harper & Scinto

[57] ABSTRACT

Chloride ion is quantitatively determined in a sample by adding to the sample an enzyme having glucokinase activity to thereby eliminate glucose, admixing an α-amylase which has been deactivated by a chelating agent, and reacting the α-amylase with maltotetraose, maltohexaose or maltoheptaose.

9 Claims, 2 Drawing Sheets

QUANTITATIVE DETERMINATION METHOD FOR CHLORIDE IONS

BACKGROUND OF THE INVENTION

1. Field of the Invention

The present invention relates to a quantitative determination method for chloride ions in an organism which is applicable to clinical tests.

2. Description of the Prior Art

There is known a quantitative determination method for chloride ions comprising reacting an α-amylase with a chloride ion-containing sample and a substrate, such as p-nitrophenylmaltoside or starch, by utilizing the phenomenon that an α-amylase deactivated by a chelating agent is activated by chloride ions [Eur. J. Biochem. 41: 171 (1974)]. There is known another quantitative determination method for chloride ions wherein 2-chloro-4-nitrophenyl-β-D-maltoheptaoside is used as a substrate in order to simplify the process for measuring the α-amylase activity in the above quantitative determination method [Clin. Chem., 34: 552 (1988)].

As a method for measuring the activity of an α-amylase, there is known a method comprising producing maltose by using an oligosaccharide as a substrate, converting the resultant maltose into glucose and quantitatively determining the glucose obtained to thereby measure the corresponding α-amylase activity [J. Clin. Chem. Clin. Biochem., 17: 705 (1979)].

Since glucose coexisting in a sample influences a quantitative determination method for a substance in a sample, a method is disclosed in Japanese Unexamined Patent Publication No. 5-76397 wherein glucose in a sample is eliminated by using hexokinase or the like.

Out of the quantitative determination methods for chloride ions, the method using a synthetic substrate such as 2-chloro-4-nitrophenyl-β-D-maltoheptaoside for measuring the activity of an α-amylase must use the two-point calibration method because linearity in calibration curves is hard to obtain. The known method by using starch as a substrate for an α-amylase reaction and measuring the reaction product, i.e. a reducing sugar such as glucose and maltose, cannot accurately determine the amount of chloride ions when a blood sample is used, because glucose and maltose are present in blood. Therefore, if a method of newly using a maltooligosaccharide as a useful substrate for an α-amylase reaction is employed, it will be impossible to achieve an accurate determination because of the interference of glucose and the like present in blood.

SUMMARY OF THE INVENTION

It is an object of the invention to provide a quantitative determination method for chloride ions which can accurately determine the amount of chloride ions even when blood is used as a sample.

DETAILED DESCRIPTION OF THE PREFERRED EMBODIMENTS

Figure 1:
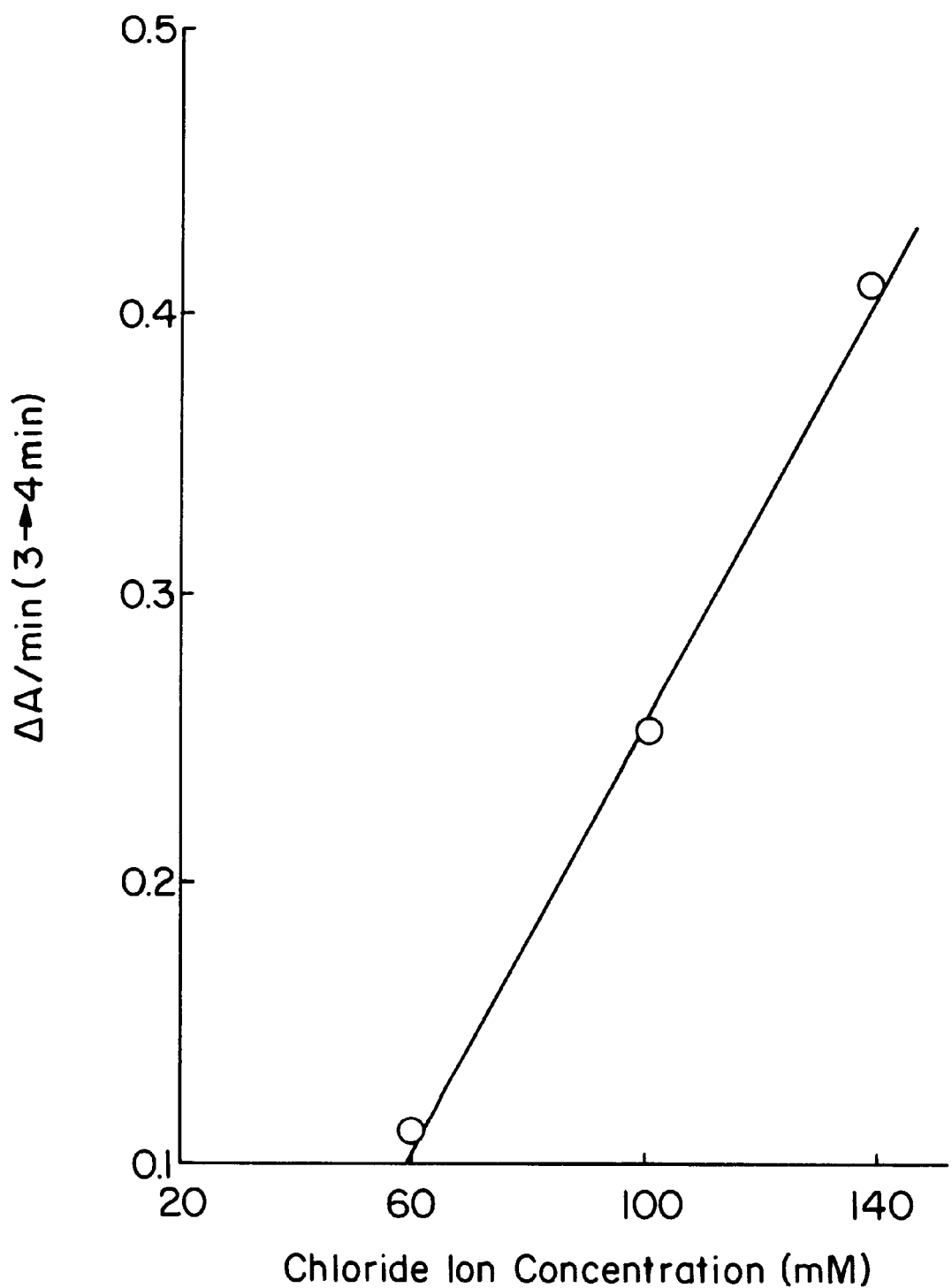
FIG. 1 is a calibration curve using maltopentaose as a substrate.

The method of the invention for quantitative determination of chloride ions relates to a method of determining, in an aqueous medium, chloride ions in a sample by using an α-amylase which has been deactivated by a chelating agent. The method of the present invention is characterized by adding to a sample in advance adenosine triphosphate and an enzyme having glucokinase activity to thereby eliminate glucose in the sample, deactivating the enzyme having glucokinase activity and determining the amount of glucose produced by a reaction of α-amylase activated by the chloride ions using an oligosaccharide as a substrate for the reaction.

The method of the invention has been achieved based on the following finding that, in the above method of determining in an aqueous medium chloride ions in a sample by using an α-amylase which has been deactivated by a chelating agent, the sample is pretreated, the oligosaccharide is used as substrate and the α-amylase activity activated by the chloride ion is determined by measuring the amount of glucose as a final product, the amount of chloride ions can be accurately determined. In particular, the method for the pretreatment of a sample has been established based on the following finding that a more accurate determination of chloride ions can be achieved by adding, to a sample, not only an enzyme having glucokinase activity for elimination of glucose in a sample but also an enzyme-inhibitor in order to prevent the enzyme having glucokinase activity from interfering the glucose determination system.

The method for the pretreatment of a sample as described above comprises eliminating glucose in a sample by adding to the sample in advance adenosine triphosphate and an enzyme having glucokinase activity and then deactivating the enzyme having glucokinase activity with an inhibitor of the enzyme such as a chelating agent or the like. As a result of the pretreatment, glucose which interferes with the quantitative determination of chloride ions is removed.

Further, in the present invention, there is provided a quantitative determination method for chloride ions which is not influenced even when maltose coexists in a sample, the method being achieved by appropriately selecting the kind of α-amylase and the kind of oligosaccharide as a substrate thereof.

In the present invention, the method of determining, in an aqueous medium, chloride ions in a sample by using an α-amylase which has been deactivated by a chelating agent means a method wherein, in an aqueous medium, an α-amylase which has been deactivated by mixing with a chelating agent and is re-activated by the chloride ions in a sample decomposes the substrate and the amount of a decomposed-product is measured to determine the amount of the corresponding chloride ions.

In the present invention, "an aqueous medium" means a liquid containing water, such as buffer and physiological saline. As examples of the buffer, tris(hydroxymethyl)aminomethane-nitrate buffer, tris(hydroxymethyl)aminomethane-sulfate buffer, phosphate buffer, acetate buffer, succinate buffer, phthalate buffer, borate buffer, glycine buffer, barbital buffer, Good's buffer and the like may be enumerated. The pH of the buffer is 6–9.5 and the concentration is 50–500 mM.

As a sample containing chloride ions, any sample may be used as long as it is miscible with an aqueous medium. For example, biosamples such as whole blood and cells, though which are difficult to quantitatively determine by the ion electrode method may be enumerated.

As an α-amylase, any enzyme belonging to the enzyme number EC. 3.2.1.1 may be used. Animal-derived α-amylases taken from porcine pancreas, human saliva and the like or enzymes produced by modifying those amylases by genetic engineering techniques may be enumerated. In the present invention, it is preferably to use a porcine pancreas-derived α-amylase because, when maltoheptaose, maltohexaose or maltotetraose is used as an oligosaccharide substrate, the enzyme decomposes the substrate into only maltotriose and glucose, and not into maltose; thus, an elimination operation for maltose is not required.

As a chelating agent, ethylenediaminetetraacetic acid (EDTA), 2-hydroxyethylethylenediaminetriacetic acid (HEDTA), ethylene glycol-bis(2-aminoethyl ether) tetraacetic acid (EGTA), diethylenetriaminepentaacetic acid (DTPA), 1, 2-diaminocyclohexanetetraacetic acid (DCTA) and the like may be enumerated.

As an oligosaccharide used as a substrate for an α-amylase, maltooctaose, maltoheptaose, maltohexaose, maltopentaose, maltotetraose and the like may be enumerated. When an oligosaccharide is decomposed by an α-amylase to produce maltose as well as glucose, an enzyme of which the substrate is maltose may be added, if necessary, to thereby convert maltose into glucose. Among oligosaccharides, maltoheptaose, maltohexaose and maltotetraose are selectively decomposed into glucose by a porcine pancreas-derived α-amylase and are not decomposed into glucose by a human amylase contaminated in a sample. Therefore, use of these oligosaccharides is preferable in the present invention.

As to a quantitative determination method for glucose, any method for determining the amount glucose may be used. For example, a method wherein glucose is converted into glucosone or gluconic lactone by pyranose oxidase or glucose oxidase, respectively, and the hydrogen peroxide generated is quantitatively determined with a peroxidase and a coloring reagent [Ann. Clin. Biochem., 6: 24 (1969)] or a method wherein glucose is converted into gluconic lactone by glucose dehydrogenase and the amount converted from NAD(P) to NAD(P)H is determined [Z. Kin. Chem. Klin. Biochem., 13: 101 (1975)] may be used.

As a coloring reagent, for example, a combination of 4-aminoantipyrine with N-ethyl-N-(3-methylphenyl)-N'-acetylethylenediamine (EMSA) or the like may be used.

In the quantitative determination method for glucose mentioned above, when endogenous glucose or maltose coexists in a sample, such glucose or maltose gives an influence upon the determined value of chloride ions. Therefore, as a pretreatment process for the above determination method, adenosine triphosphate, an enzyme having glucokinase activity and, if necessary, the above-mentioned enzyme of which the substrate is maltose are added to a sample in advance to thereby eliminate glucose or maltose in a sample and then a chelating agent is added to the sample to deactivate the enzyme having glucokinase activity so that this enzyme coexisting in the sample does not inhibit the process of quantitative determination of chloride ions.

As an enzyme having glucokinase activity, any enzyme may be used as long as it has an activity to convert glucose into glucose-6-phosphoric acid. For example, hexokinase (EC. 2.7.1.1) derived from animals (such as erythrocytes and a liver) or microorganisms, hexokinase type IV (EC. 2.7.1.2) derived from animals (such as a liver) or microorganisms (such as bacteria and yeast) and the like may be enumerated.

As a chelating agent which is used for deactivating an enzyme having glucokinase activity, chelating agents similar to those used for deactivating an α-amylase may be used. For example, EDTA, HEDTA, EGTA, DTPA, DCTA and the like may be enumerated.

As an enzyme of which the substrate is maltose, any enzyme which can convert maltose into glucose, such as maltose phosphorylase (EC. 2.4.1.8) or α-glucosidase (EC. 3.2.1.20), may be used. When maltose phosphorylase is used, phosphate ions are added to a reaction solution together with this enzyme if phosphate buffer is not used. As a source of these phosphate ions, inorganic phosphoric acid, monopotassium phosphate, dipotassium phosphate, monosodium phosphate, disodium phosphate and the like may be enumerated. It should be noted that when a porcine pancreas-derived α-amylase is used together with maltoheptaose, maltohexaose or maltotetraose as a substrate, it is not necessary to add an enzyme of which the substrate is maltose because maltose will not be generated.

Preferred embodiments of the quantitative determination method of the invention for chloride ions will be described below.

To an aqueous medium (pH 6–9.5), an enzyme having glucokinase activity (1–4 U/ml), adenosine triphosphate (ATP)(5–20 mM), magnesium ions (2–25 mM) and, if necessary, an enzyme of which the substrate is maltose (when maltose phosphorylase is used, 4–20 U/ml of this enzyme and 300 mM or more of phosphoric acid are added against 1 g/dl of maltose; when α-glucosidase is used, 100–300 U/ml of this enzyme is added against 1 g/dl of maltose)are added to prepare a pretreatment solution. A sample containing chloride ions is added to the pretreatment solution and then reacted at 25–40° C., preferably 37° C., for 1–30 minutes, preferably 3–5 minutes.

An oligosaccharide (2–10 mM in the reaction solution) may be added to the pretreatment solution in advance or may be added after the completion of the pretreatment reaction. Further, a chelating agent (10–50 mM in the reaction solution) and an α-amylase which has been deactivated by a chelating agent (20–100 U/ml in the reaction solution) are added to the solution and reacted at 8–50° C. The oligosaccharide (the substrate) is decomposed into maltose, glucose and maltotriose through an α-amylase reaction. When maltose is generated, the maltose is decomposed into glucose by the above-mentioned enzyme of which the substrate is maltose. By determining the amount of the resultant glucose by the method described above, the amount of the corresponding chloride ions can be determined. A chelating agent which inhibits glucokinase activity also deactivates α-amylase. Therefore, if a solution is prepared in advance by adding an α-amylase (20–100 U/ml in the reaction solution) and reagents for the quantitative determination of glucose such as glucose oxidase and EMSA to an aqueous medium containing a chelating agent (10–50 mM in the reaction solution) and the prepared solution is added to the pretreatment solution for a sample, the amount of chloride ions can be simply determined.

To the reaction solution, there may be added albumin, flavin adenine dinucleotide (FAD) which is a coenzyme of pyranose oxidase, glycerol, a chloride ion-free surfactant such as polyethylene glycol mono-p-isooctylphenyl ether and condensation products of polyoxyethylene and polyoxypropylene, a solubilizer such as sodium nitrate and sodium sulfate, and stabilizer such as potassium nitrate and potassium sulfate. Further, by adding glucose (0.08–0.2 mg/ml) to the pretreatment solution, a blank absorption can be eliminated.

With respect to the enzymes used in the present invention, for example, maltose phosphorylase (EC. 2.4.1.8), α-glucosidase (EC. 3.2.1.20) and hexokinase (EC. 2.7.1.1) or hexokinase type IV [glucokinase (EC. 2.7.1.2)] as an enzyme having glucokinase activity, commercial products are easily available for each of them.

BRIEF DESCRIPTION OF THE DRAWINGS

Figure 2:
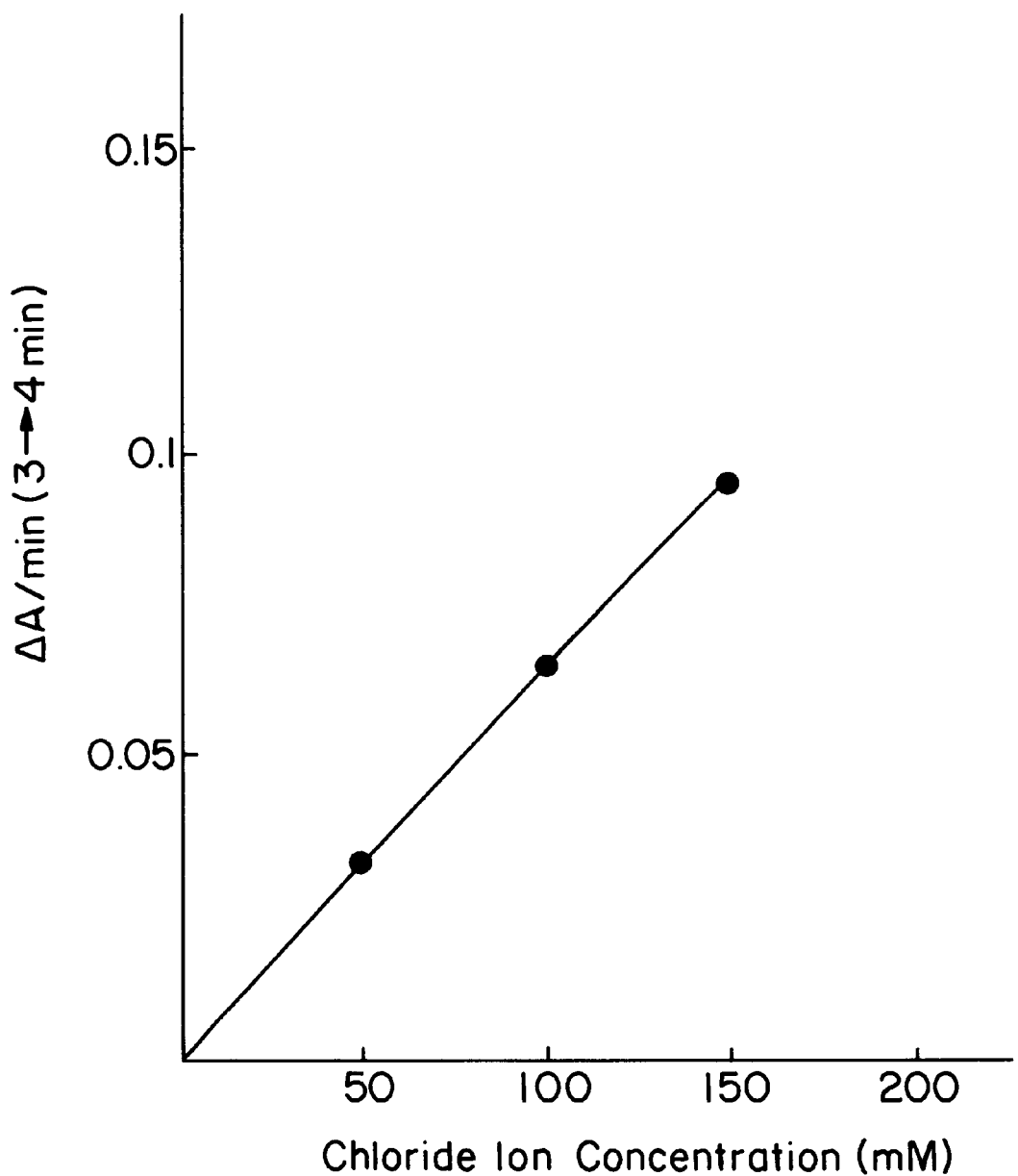
FIG. 2 is a calibration curve using maltotetraose as a substrate.

FIG. 1 is a graph showing a calibration curve obtained by using maltopentaose as a substrate. FIG. 2 is a graph showing a calibration curve obtained by using maltotetraose as a substrate.

BEST MODE FOR CARRYING OUT THE INVENTION

The present invention will be described in more detail with reference to the following Examples, which should not be construed as limiting the scope of the invention.

EXAMPLE 1

A Method using a Porcine Pancreas α-amylase and Maltopentaose (1) Preparation of Standard Solutions for Obtaining a Chloride Ion Calibration Curve Sodium chloride (Wako Pure Chemicals) was diluted with distilled water to prepare standard solutions for obtaining a chloride ion calibration curve so that the final concentrations in the reaction solution become 60, 100 and 140 mM.

(2) Quantitative Determination of Chloride Ions

To a test tube, 0.10 ml of the standard solution for obtaining a chloride ion calibration curve, 0.10 ml of an aqueous glucose solution (1 g/dl) and 0.10 ml of an aqueous maltose solution (1 g/dl) were added. Then, 2.0 ml of 350 mM phosphate buffer (pH 6.8, 25° C.) containing 7 U/ml maltose phosphorylase (Kyowa Medex), 2.4 U/ml hexokinase (Oriental Yeast), 10 mM maltopentaose (Kyowa Medex), 0.5 mM 4-aminoantipyrine, 2.5 mM magnesium sulfate and 10 mM ATP (Oriental Yeast) was added thereto. The test tube was put in a constant-temperature water bath at 37° C. and incubated for 5 minutes, to thereby eliminate maltose and glucose.

Thereafter, to a solution (25° C.) containing 20 g/l monopotassium phosphate and 18 g/l EDTA, of which the pH has been adjusted to 6.8 with sodium hydroxide, a coloring solution containing 50 U/ml porcine pancreas α-amylase (Boehringer Mannheim Yamanouchi), 30 U/ml glucose oxidase (Wako Pure Chemicals), 2.2 mM EMSA and 1 mM potassium nitrate was added and incubated at 37° C. Then, 1 ml of this solution was added to the solution prepared above. After stirring, changes in absorbance at 555 nm were measured with a spectrophotometer (Model UV3400, Hitachi). The calibration curve obtained is shown in FIG. 1.

EXAMPLE 2

A Method using a Porcine Pancreas α-amylase and Maltotetraose (1) Preparation of Standard Solutions for Obtaining a Chloride Ion Calibration Curve Sodium chloride (Wako Pure Chemicals) was diluted with distilled water to prepare standard solutions for obtaining a chloride ion calibration curve so that the final concentrations in the reaction solution become 50, 100 and 150 mM.

(2) Quantitative Determination of Chloride Ions

To a test tube, 0.05 ml of the standard solution for obtaining a chloride ion calibration curve, 0.05 ml of an aqueous glucose solution (1 g/dl) and 0.05 ml of an aqueous maltose solution (2 g/dl) were added. Then, 2.0 ml of 100 mM phosphate buffer (pH 6.6, 25° C.) containing 2.4 U/ml hexokinase (Oriental Yeast), 7.5 mM maltotetraose (Wako Pure Chemicals), 0.5 mM 4-aminoantipyrine, 5 mM magnesium sulfate and 10 mM ATP (Oriental Yeast) was added thereto and incubated at 37° C. for 5 minutes, to thereby eliminate glucose.

Thereafter, to a solution (25° C.) containing 20 g/l monopotassium phosphate and 36 g/l EDTA, of which the pH has been adjusted to 6.6 with sodium hydroxide, a coloring solution containing 70 U/ml porcine pancreas α-amylase (Boehringer Mannheim Yamanouchi), 30 U/ml glucose oxidase (Wako Pure Chemicals), 2.2 mM EMSA and 1 mM potassium nitrate was added and incubated at 37° C. Then, 1 ml of this solution was added to the solution prepared above. After stirring, changes in absorbance at 555 nm were measured with a spectrophotometer (Model UV3400, Hitachi). The calibration curve obtained is shown in FIG. 2. In addition, a serum whose chloride ion concentration was 105 mM as determined by coulometric titration was measured for its chloride ion concentration according to the above method. As a result, the chloride ion concentration was found 104 mM.

According to FIG. 2, the calibration curve passes through the origin and thus it is possible to carry out a one-point calibration. Further, it has been demonstrated that the method of the invention is an excellent determination method because; the absorption of blank is little and the method is not influenced by maltose nor endogenous, saliva-derived or pancreas-derived amylase in a sample.

According to the present invention, a quantitative determination method for chloride ions is provided which is not influenced by glucose, maltose and the like coexisting in a sample and is excellent in determination accuracy. The quantitative determination method of the invention for chloride ions is useful as a clinical test.

We claim:

1. A method for quantitatively determining chloride ion in a sample, comprising the steps of:
    (1) admixing (i) an enzyme having a glucokinase activity, (ii) adenosine triphosphate and (iii) an aqueous medium comprising said sample;
    (2) reacting said sample with said enzyme to eliminate any glucose coexisting in said sample, to obtain mixture (A);
    (3) admixing mixture (A) with (i) an α-amylase which has been deactivated by a chelating agent and (ii) a chelating agent to deactivate the enzyme having a glucokinase activity, to obtain mixture (B);
    (4) reacting said α-amylase of mixture (B) with a naturally occurring oligosaccharide selected from the group consisting of maltotetraose, maltohexaose and maltoheptaose;
    (5) determining an amount of glucose produced in the reaction of step (4); and
    (6) correlating said amount of glucose with a quantity of chloride ion in said sample.

2. The method of claim 1, wherein said α-amylase is derived from porcine pancreas.

3. The method of claim 1, wherein said enzyme having a glucokinase activity is hexokinase.

4. The method of claim 4, wherein said enzyme having a glucokinase activity is hexokinase type IV.

5. The method of claim 1, wherein chloride ion is determined without using two-point calibration.

6. The method of claim 1, wherein a concentration of said chelating agent in step (3) is 10–50 mM.

7. The method of claim 1, wherein said chelating agent is selected from the group consisting of ethylenediaminetetraacetic acid (EDTA), 2-hydroxyethylethylenediaminetriacetic acid (HEDTA), ethylene glycol-bis(2-aminoethyl ether)tetraacetic acid (EGTA), diethylenetriaminepentaacetic acid (DTPA) and 1,2-diaminocyclohexanetetraacetic acid (DCTA).

8. The method of claim 1, wherein said oligosaccharide is added to mixture (B) in a concentration of 2–10 mM.

9. The method of any one of claims 1–8, wherein glucose is correlated with chloride ion using a calibration curve that substantially passes through its origin.

* * * * *

UNITED STATES PATENT AND TRADEMARK OFFICE
CERTIFICATE OF CORRECTION

PATENT NO. : 5,962,248
DATED : October 5, 1999
INVENTOR(S) : TOSHIO TADANO ET AL.

It is certified that error appears in the above-identified patent and that said Letters Patent is hereby corrected as shown below:

COLUMN 2:

Line 26, "the" should read --with the--; and
Line 61, "though" should read --and other samples--.

COLUMN 3:

Line 3, "preferably" should read --preferable--; and
Line 29, "amount" should read --amount of--.

COLUMN 5:

Line 4-11 should be deleted.

Signed and Sealed this

Thirteenth Day of March, 2001

Attest:

NICHOLAS P. GODICI

Attesting Officer      Acting Director of the United States Patent and Trademark Office